United States Patent [19]

Cremer

[11] Patent Number: 5,693,875
[45] Date of Patent: Dec. 2, 1997

[54] PROCESS FOR MEASURING THE TEMPERATURE OF METALLIC WORKPIECES AND THEIR SOLID CONTENT IN A PARTIALLY SOLIDIFIED STATE

[75] Inventor: Ralf Cremer, Aachen, Germany

[73] Assignee: EFU Gesellschaft für Ur-/Umformtechnik mbH, Germany

[21] Appl. No.: 640,976

[22] PCT Filed: Nov. 7, 1994

[86] PCT No.: PCT/DE94/01311

§ 371 Date: May 9, 1996

§ 102(e) Date: May 9, 1996

[87] PCT Pub. No.: WO95/13532

PCT Pub. Date: May 18, 1995

[30] Foreign Application Priority Data

Nov. 9, 1993 [DE] Germany ............... 43 38 200.2

[51] Int. Cl.$^6$ ................. G01N 25/00; G01K 7/36
[52] U.S. Cl. ........................... 73/61.71; 374/43
[58] Field of Search ................. 73/61.71; 374/43

[56] References Cited

U.S. PATENT DOCUMENTS

| | | | |
|---|---|---|---|
| 3,222,917 | 12/1965 | Roth | 374/5 |
| 3,981,175 | 9/1976 | Hammond, III et al. | 374/10 |
| 4,381,154 | 4/1983 | Hammond, III | 374/43 |
| 4,385,843 | 5/1983 | Hammond, III et al. | 374/43 |
| 5,052,819 | 10/1991 | Baratta | 374/43 |

FOREIGN PATENT DOCUMENTS

| | | |
|---|---|---|
| 291422 | 6/1991 | Germany. |
| 2953 | 9/1982 | WIPO ............ 374/43 |

OTHER PUBLICATIONS

Pätzold et al., "Determining the Solid Portion in Aluminum Alloys During Thixocasting by Means of New Eddy Current Sensor", Giesserei, No. 4, 1993, pp. 110–112.

Primary Examiner—Hezron E. Williams
Assistant Examiner—Daniel S. Larkin
Attorney, Agent, or Firm—Staas & Halsey

[57] ABSTRACT

The invention relates to a measuring process for the indirect measurement of the temperature and solids content of metal workpieces during inductive heating. To this end, in a coupled coil system comprising a heating coil, the effect of alterations in the electrical conductivity of the workpiece is determined by the combination, using circuit-mathematical techniques, of a signal tapped from the exploring coil with a reference signal from the driving coil. The two signals are combined in such a way that the measurement signal obtained depends solely on the phase shift between the reference signal and the exploring coil signal and/or on the quotient of the amplitude values of the reference signal and the exploring coil signal. This facilitates measurement which is independent of the amplitude of the alternating electromagnetic field created by the driving coil. With the aid of alloy- and geometry-specific calibration curves, the measurement signal can be associated with the particular value being sought (temperature or solids content). In addition, the measurement signal can be used for the continual adjustment of the heating in order to regulate the target value.

17 Claims, 5 Drawing Sheets

PROCESS FOR MEASURING THE TEMPERATURE OF METALLIC WORKPIECES AND THEIR SOLID CONTENT IN A PARTIALLY SOLIDIFIED STATE

BACKGROUND OF THE INVENTION

The invention relates to a process for measuring the temperature of metallic workpieces and their solid content in a partially solidified state and a device, suitable for performing the procedure comprising a driving coil, an exploring coil and an electronic device for comparing the signals received from the driving coil and the exploring coil.

A variety of production processes demand as precise an understanding as possible of the temperature or the inner structural condition of a metallic workpiece. Whilst temperatures and related phase changes are of central importance in processes during which solid metallic materials are processed or refined (such as heat treatment, deformation, inductive hardening or such like), shaping in a partially solidified state (such as thixo-pouring, thixo-forging) center not only on defining the temperature, but also more significantly on accurately maintaining the required ratios of solid and liquid phases.

The object of the invention is a process for measuring a signal which depends on the electrical conductivity of the metallic workpiece and for evaluating this signal in order to be able to draw conclusions on the temperature or on the ratios of solid and liquid phases during partial melting.

Below the solidus temperature, there is a direct correlation in metals between electrical conductivity and temperature. Between the solidus temperature and the liquidus temperature, the ratios of solid and liquid phases generally cannot be recorded by measuring the temperature because the temperature can remain constant during melting and solidification until such time as the fusion heat is added or drawn off. Moreover, the temperature of the phase transition point is also affected by the heating or cooling rates. However, electrical conductivity is dependent, among other things, on the ratios of solid and liquid phases and can, thus, be used for calculating these ratios.

It is an established fact (*GieBerei* 80 (1993) no. 4/22nd Feb., pp. 111, 112) that a non-contact measurement of the electrical conductivity can also provide information in the solidus liquidus interval on the phase transition points and on the ratios of the solid and liquid phases in the workpiece under examination.

A separate driving coil is used there for the heating process. If the workpiece is heated up inductively, the heating device must be switched off in order to perform the measurement; otherwise, the field induced by the heating power would invalidate the measurement. At the specified measurement frequency of 1 kHz, the measurement is limited to an area of the workpiece near the surface because of the skin effect.

SUMMARY OF THE INVENTION

The present invention now entails defining a process and creating a device which is suitable for performing the process in order, principally, to avoid the above disadvantages and to find a simple and reliable solution.

This task is solved in the present invention in the form of a process as mentioned at the start, characterised in that the workpieces are sent a driving signal (i.e. reference signal) which turns into a measurement signal in an exploring coil situated near the workpiece; the measurement signal is compared with the driving signal, the driving signal is induced by an induction coil which serves to heat up the workpiece and surrounds same, a phase shift is defined between these two signals and/or a quotient is defined from the amplitude-related values of the two signals, a calibration curve relating to the inter-dependence between the phase shift and/or the value of the quotient on the one hand and the temperature of and percentage of solid matter in this type of workpiece on the other hand is plotted applying conventional methods, and in other workpieces of this type, the temperature and the percentage of solid matter are calculated from the phase shift and/or the value of the quotient by referring to the calibration curve.

The process in accordance with the invention records the condition of the entire inductively heated material, even during inductive heating. In this case, the heating coil i.e. driving coil, an exploring coil, and the workpiece combine to form a coupled system of coils. As they pass through the workpiece, the electromagnetic components of the electromagnetic field generated by the heating coil experience attenuation and phase shift, which is determined by the electrical conductivity and the permeability of the workpiece (the latter only applies in the case of ferromagnetic material). The phase shift and/or attenuation can be calculated by combining the two signals, which can be tapped at the driving coil and at the exploring coil; the signals are combined here by means of circuit-mathematical techniques. The amplitude of the signals tapped at the exploring coil is determined primarily by the heating output and the attenuation.

It has been discovered that the phase shift and the value of the quotient of the two signals is only determined by the electrical and magnetic data on the material of the workpiece, and, contrary to amplitude, not by the induced inductive heating output. Consequently, in the process in accordance with the invention, the driving signal and the exploring coil signals are combined by means of circuit-mathematics in such a way that the measurement signal derived only depends upon the phase shift between the driving signal and the exploring coil signal and/or the value of the quotient calculated from the driving signal and the exploring coil signal.

After recording an alloy-specific and geometry-specific calibration curve, the temperature of the workpiece up to the solidus temperature or the ratios of solid and liquid phases between the solidus and liquidus temperature can be determined applying the process in accordance with the invention. Given the fact that the measurement signal acts independently of the heating output, it can, if necessary, be used directly for establishing a way of continuously regulating the heating process.

The process in accordance with the invention can also be devised in such a manner that the quotient is determined from the effective values of the two signals.

The process in accordance with the invention can also be devised in such a manner that the incoming frequency of the driving signal lies between 50 Hz and 10 kHz. This means, in effect, that the measurement procedure can be integrated into existing heating systems without any difficulty.

The process in accordance with the invention can also be devised in such a manner that the driving frequency is kept constant. Consequently, a calibration curve for a specific workpiece can be incorporated into other inductive heating systems with a fixed incoming frequency.

The process in accordance with the invention can also be devised in such a manner that the voltage induced in the exploring coil is selected to serve as the exploring coil signal. By virtue of this measure and a high-resistance processing of this voltage, the power in the sensor circuit is kept virtually constant and loss-free. Consequently, the effects which the sensor circuit has on the driving signal and the effect of temperature in the exploring coil circuit are negligible.

The process in accordance with the invention can also be devised in such a manner that the reference signal is derived from the heating coil's current. This ensures that the measurement signal is not affected by the impedance which is formed by the driving coil, the workpiece, and the exploring coil.

The task is solved in the present invention by a process of the type mentioned at the start, characterised in that the driving coil serves as the induction coil which heats and surrounds the workpiece, and that the exploring coil is embedded in fireproof material to safeguard it against mechanical stress and mechanical displacement and is mounted on a support which can be positioned with the workpiece to be measured within the field of the induction coil. Thus, the exploring coil does not require additional cooling.

The device in accordance with the invention can also be advantageously designed in such a manner that the exploring coil is attached to a ceramic plate or to a ceramic ring, embedded on the front surface of a tool or support used for pushing the workpiece into a shaping chamber. A device such as this is particularly suitable for coping with high mechanical stress on the exploring coil.

The device in accordance with the invention can also be advantageously designed in such a manner that the exploring coil is integrated into a support. This means that the workpiece and the exploring coil can be positioned in relation to one another with precision and reproducibly in the driving field.

The device in accordance with the invention can also be advantageously designed in such a manner that the exploring coil is arranged within an electrical insulator, positioned as closely as possible to the front of the workpiece. This ensures that the measurement signal has a high resolution.

The device in accordance with the invention can also be advantageously designed in such a manner that the exploring coil is thermally insulated against the workpiece. Thus, the exploring coil does not require additional cooling.

The device in accordance with the invention can also be advantageously designed in such a manner that the turns of the exploring coil are arranged within the profile of the workpiece. This benefits the resolution of the measurement signal.

The device in accordance with the invention can also be advantageously designed in such a manner that the turns are arranged at a constant distance from the contour of the front of the workpiece, within the profile of this front. This means that particular areas of the workpiece can be analysed and the resolution of the measurement signal benefited.

The device in accordance with the invention can also be advantageously designed in such a manner that the exploring coil takes the form of a single or multiple ring-shaped wire coil. This simple and compact design means that the exploring coil can be integrated particularly easily into existing inductive heating devices.

BRIEF DESCRIPTION OF THE DRAWINGS

Some of the design variants of the invention are described in the following part of the description with the aid of drawings.

DESCRIPTION OF THE PREFERRED EMBODIMENTS

Figure 1:
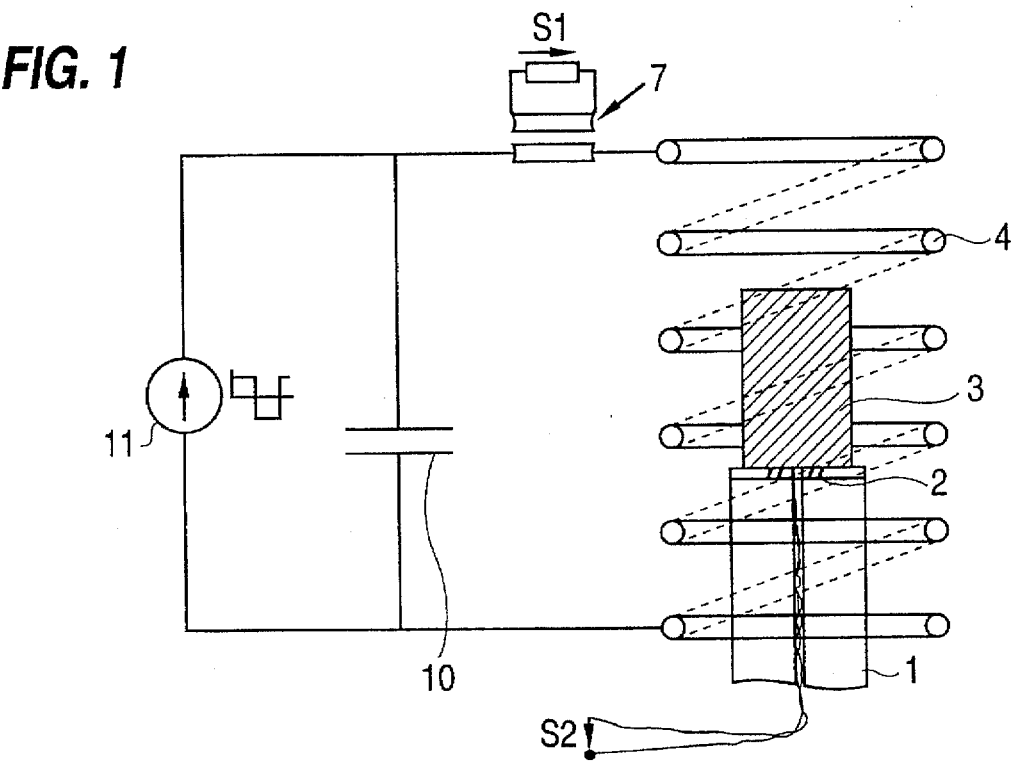
FIG. 1 is a basic arrangement of the signal-registering elements in an inductive heating system for performing the process in accordance with the invention.

Example 1:

FIG. 1 illustrates a basic arrangement of signal-registering elements in an inductive heating system for performing the process in accordance with the invention. A support [1] acts as a receptacle for an exploring coil [2] and serves to accurately position the exploring coil [2] on the front of a workpiece [3] and/or to position the workpiece [3] and exploring coil [2] within the field of a driving coil [4]. Before the workpiece [3] rises to the liquidus temperature, the support material only experiences very marginal changes in terms of its specific electrical and mechanical properties by comparison with the electromagnetic properties of the workpiece [3]. The type of material used for the support depends essentially on the mechanical stress which has to be endured by the support [1] and exploring coil [2].

Figure 7:
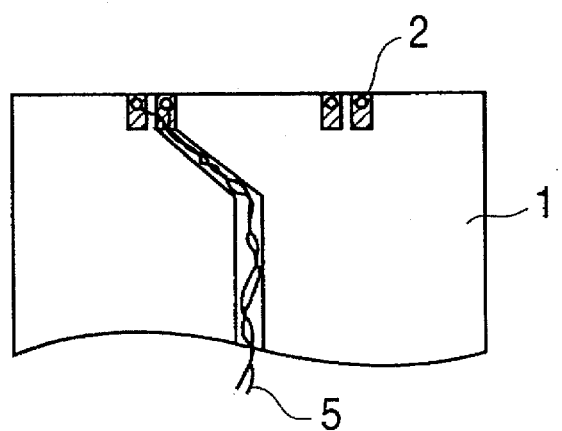
FIGS. 7 and 10 are designs of the exploring coil in which the coil is embedded in a support made from insulating material.

In the present example, as illustrated in FIG. 7, the exploring coil [2] is embedded in electrically insulating, heat-resistant material in a groove in support [1]; the support is also made from insulating material, such as pressed aluminium oxide. A supply line [5] is attached to the exploring coil [2].

Figure 2:
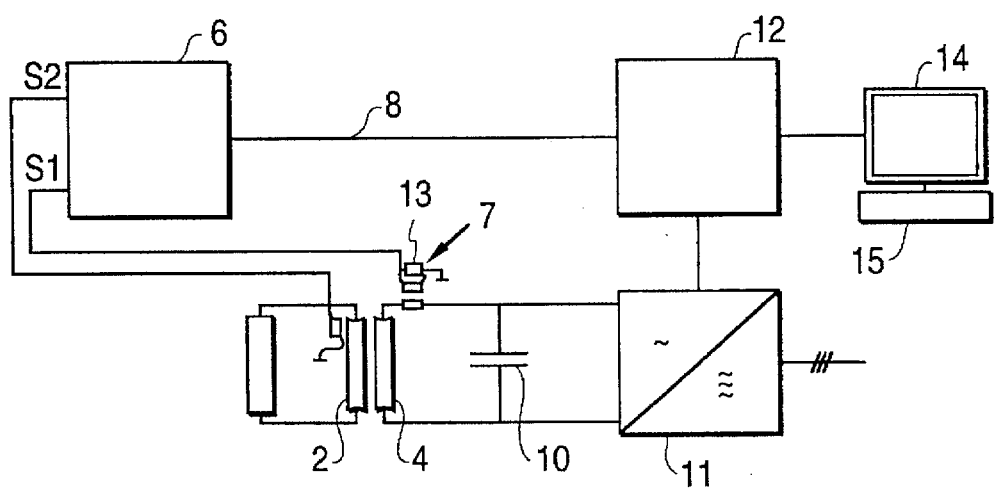
FIG. 2 is a block circuit diagram of the measurement process which is integrated within an inductive heating system.
Figure 5A:
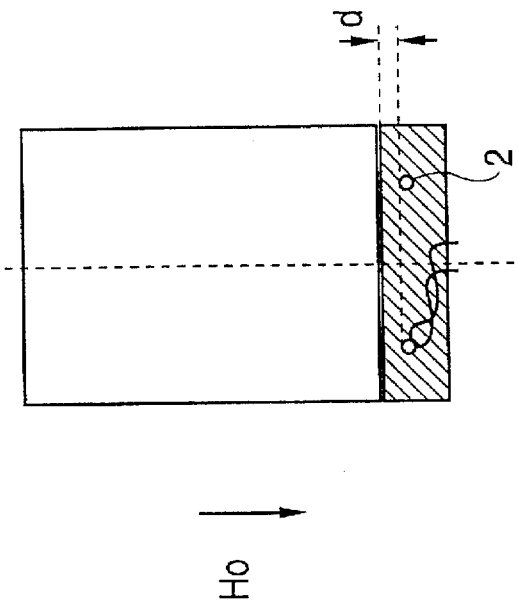
FIG. 5 is an axial view and a top view of a first design of the exploring coil in accordance with the invention.
Figure 5B:
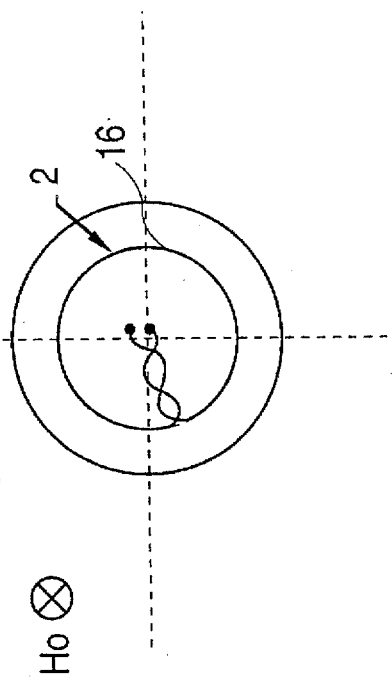

The exploring coil [2] illustrated in FIG. 5 comprises two turns which are laid on the same level in the insulating material in such a manner that the induced voltages from each winding partly compensate one another. This benefits the exploring coil signal for a phase shift comparator [6] selected here (FIG. 2).

Figure 6A:
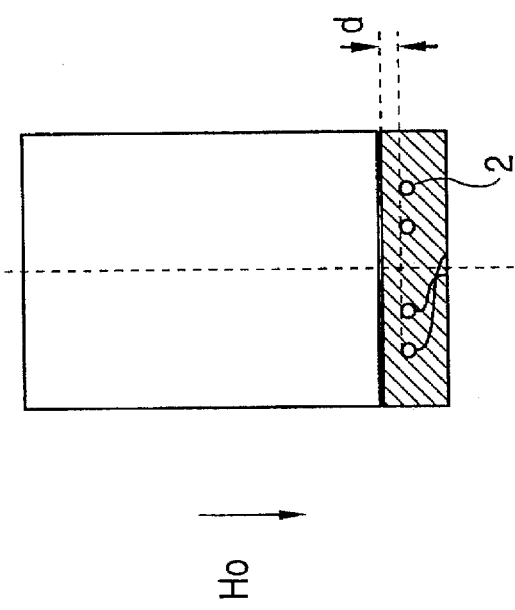
FIG. 6 is an axial view and a top view of a further design of the exploring coil in accordance with the invention.
Figure 6B:
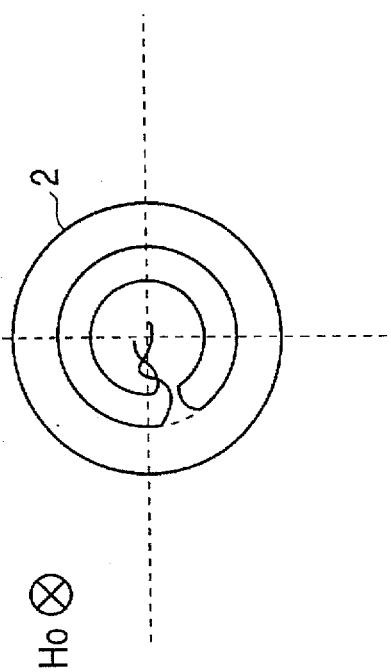

The supply lines [5] of the exploring coil [2] are insulated using a fibre-glass tube and are fed in a twisted manner through to the exploring coil [2] through a central hole which has been made in the support [1]. The arrangement comprising the support [1], the exploring coil [2], and the supply line [5] is mounted on an appropriate elevating mechanism and can be moved along a horizontal plane. The workpiece [3], for instance an AlSi7Mg bolt, is positioned on the support [1] containing the exploring coil [2] and is carried to a defined position within the electromagnetic field of the driving coil [4], which heats the workpiece [3]. The gap, d, (FIG. 5 and FIG. 6) between the workpiece [3] and the exploring coil 2 should be kept as small as possible, whilst adhering to the insulation requirements, in order to achieve as high a resolution as possible from the measurement signal. The resolution of the measurement signal is also enhanced substantially by the fact that the contour of the exploring coil [2] does not project past the front of the workpiece [3] (FIG. 5 and FIG. 6). In addition, the outside contour of the exploring coil [2] should run parallel to the front contour of the workpiece [3].

Applying the law of induction, a voltage [S2] is induced in the exploring coil [2] when the driving coil [4] is switched on. The reference signal [S1] from the driving coil current is registered using a tong-test instrument [7] (FIG. 1) and is converted into a voltage signal. The reference signal [S1] and the voltage signal [S2] induced in the exploring coil [2] are each guided to the phase shift comparator [6] (i.e., lock-in amplifier) (FIG. 2) via a coaxial cable. The measurement signal Um [8] is formed with the aid of the lock-in amplifier [6] and is output as direct voltage.

Figure 4:
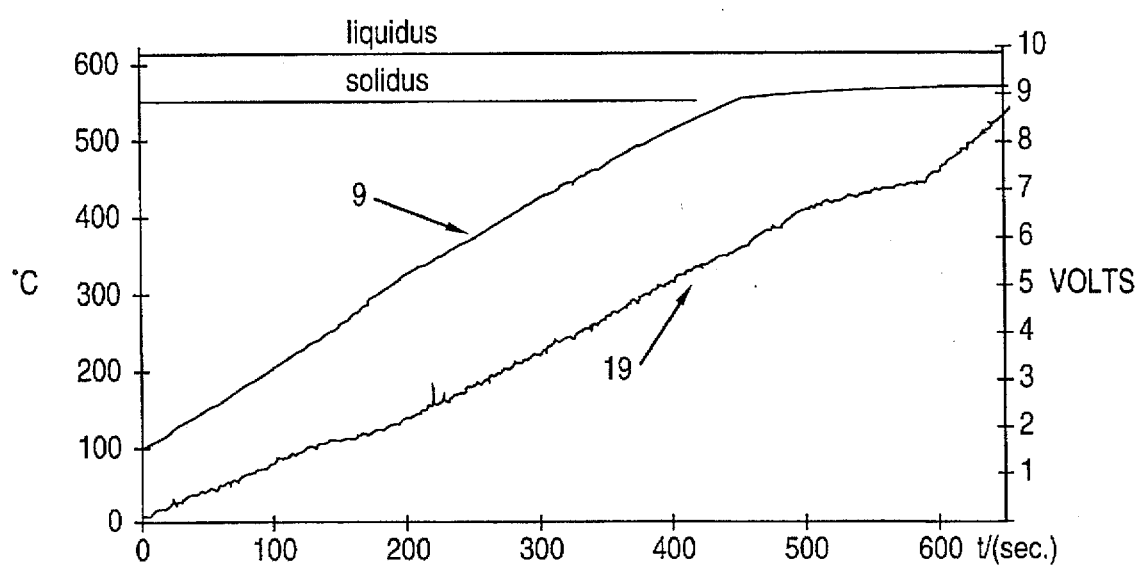
FIG. 4 is a record of measurement in which the measurement signal and, by way of comparison, the workpiece temperature are plotted over time when the workpiece is heated.

FIG. 4 illustrates a record of measurement. Curve [19] indicates the measurement signal Um in volts derived applying the process in accordance with the invention. The signal was plotted during a period of time when a workpiece [3] is heated. By way of comparison, curve [9] depicts the temperature of the workpiece [3] in °C., measured using an NiCrNi thermocouple. Thus, curve [9] serves as a calibration curve for the workpiece parameters; this means that the measurement signal Um in curve [19], with the same workpiece parameters, can be used to deduce a temperature and, in the area between the solidus line and the liquidus line, to ascertain the solid matter contents of the workpiece [3].

Figure 3:
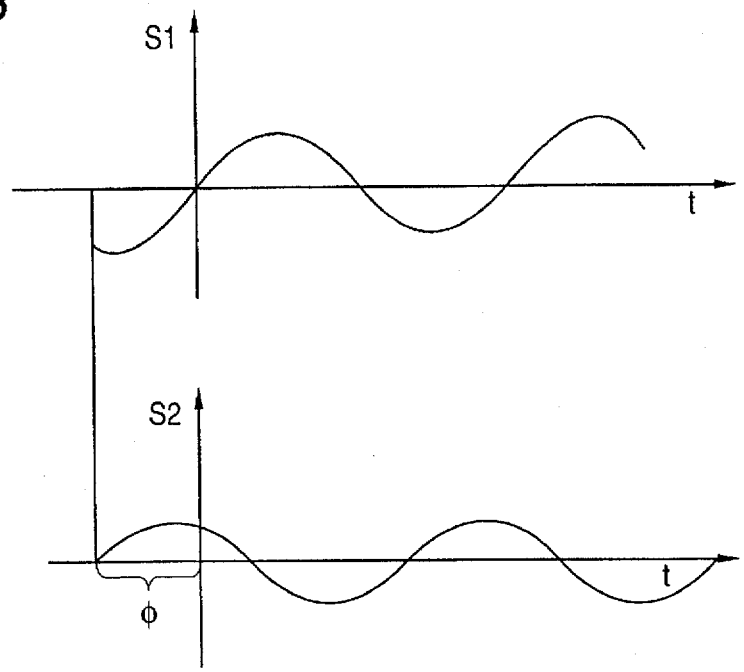
FIG. 3 is the basic pattern plotted over time by the reference signal and the exploring coil signal with the workpiece in a constant state.

FIG. 3 illustrates the basic sinusoidal patterns of the reference signal [S1] and the exploring coil signal [S2] plotted against time, t, while the workpiece [3] is in a constant state of heating.

Example 2

FIG. 2 illustrates a block circuit diagram including the electrical equivalent circuit diagram of the measurement arrangement in example 1, together with the units which generate the signals. There is a parallel resonant circuit comprising a driving coil [4] and a resonant circuit capacitor [10]; the parallel resonant circuit is supplied by a frequency converter [11], which in turn is controlled by a process control system [12]. The workpiece [3], with the driving coil [4], is regarded as the transformer, which is supplied in the primary circuit by the driving coil current and loaded in the secondary circuit with a resistance load. The exploring coil signal [S2] is registered inductively on the workpiece [3]. The reference signal [S1] is tapped using a tong-test instrument [7] and is converted into a voltage signal via a resistor [13]. These two signals are fed to the input of the phase shift comparator [6]. The measurement signal is outputted in a linear manner, depending on the phase shift of the input signals within a voltage range of 0 to 10 volts. The measurement signal Um [19] is conducted to the process control system [12]. With the aid of saved calibration curves, the heating process is monitored on the visual display unit [14] of the process control system [12] and/or is adapted using the keyboard [15] of the process control system [12] or is also regulated by the process control system [12].

The attenuation can also be measured as an alternative to measuring the phase shift. To this end, the two signals [S1] and [S2] are converted into their effective values in a suitable meter and are then divided up. In this case, the measurement signal [8] is output linked to the quotient value within a voltage range of 0 to 10 volts.

Example 3:

As already described in examples 1 and 2, the measurement process can be performed using a variety of different designs of exploring coils. An exploring coil [2] is illustrated in FIG. 6 which is particularly simple in its design. It simply comprises a turn [16], which is arranged concentrically to the front of the workpiece [3].

Figure 8:
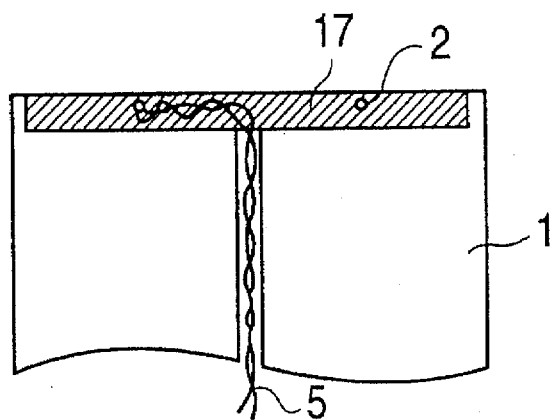
FIG. 8 is a design of the exploring coil in accordance with the invention which is capable of withstanding a high degree of mechanical stress; in this design the coil is embedded in a ceramic plate and attached to a support.
Figure 9:
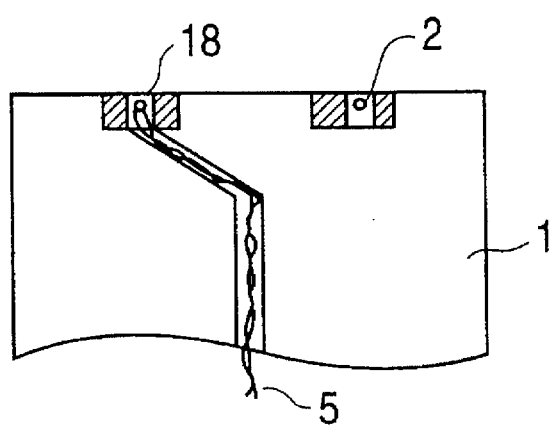
FIG. 9 is another design of the exploring coil in accordance with the invention which is capable of withstanding a high degree of mechanical stress; in this design the coil is embedded in a ceramic ring and attached to a support.

Example 4:

FIG. 8 and FIG. 9 depict designs of the exploring coil [2] which are suitable for creating the measurement process in cases where a particularly high degree of mechanical stress is exerted on the support [1] and exploring coil [2]. The support [1], with the exploring coil [2], is attached to the front of a piston on a pressure die casting machine (thixopress). In this case the support is made from nonmagnetic steel (4828, 4878, or a similar material) or from ceramic. The heated workpiece [3] is moved together with the support [1] and the exploring coil [2] into the casting chamber, whereby the exploring coil [2] is baked or embedded in a ceramic plate [17] to enable it to withstand the effects of pressure and temperature. The coil is attached to the support (glued, shrunk, or such like). The exploring coil [2] can also be embedded in a ceramic ring [18] with a hollow profile (FIG. 9). This ceramic ring [18] is securely inserted into a matching groove on the front of the support [1].

Figure 10:
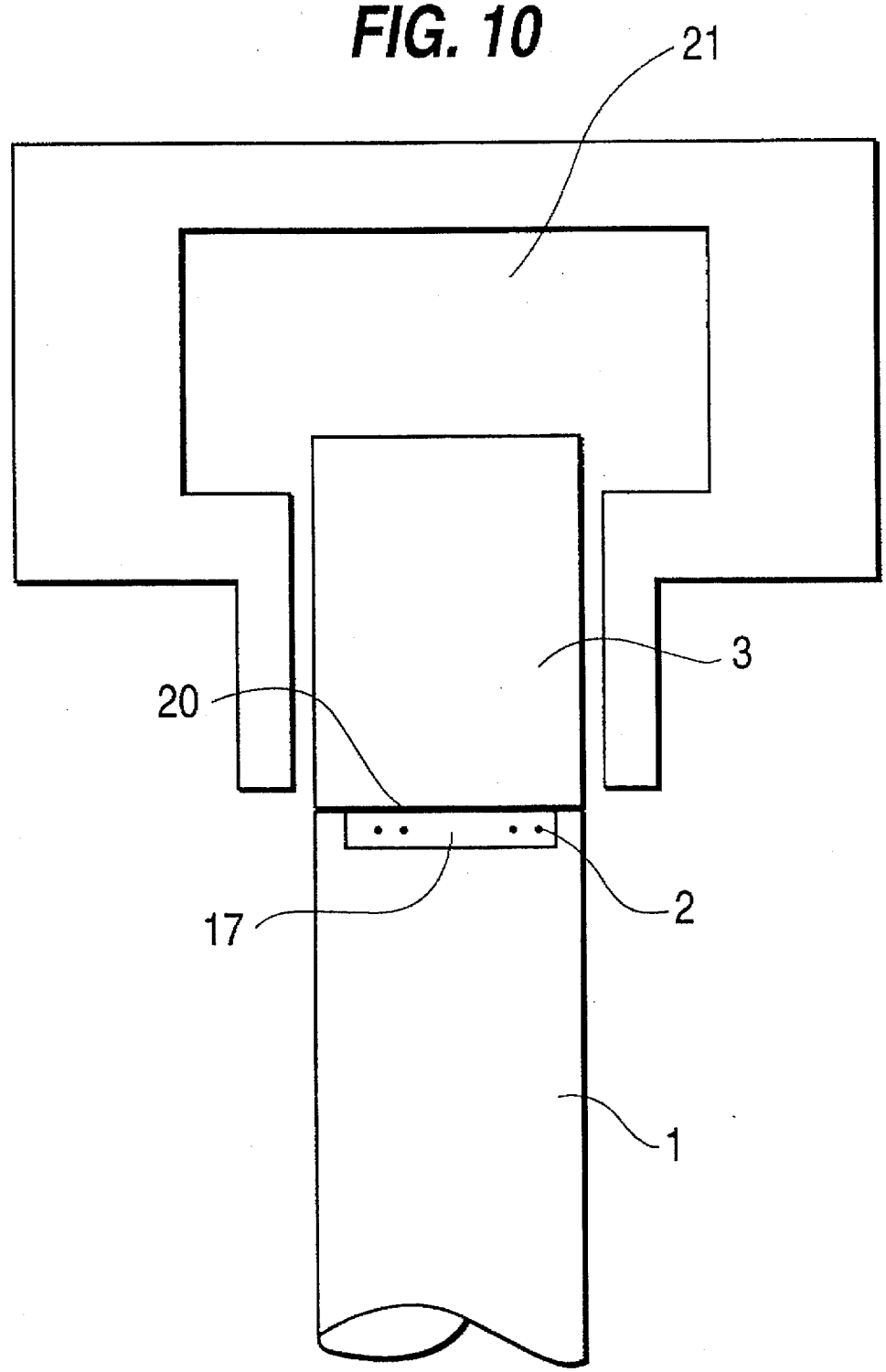

FIG. 10 illustrates a casting operation wherein the front surface [20] of the support [1] is used to push the workpiece [3] into a casting chamber [21]. In this figure the exploring coil [2] is shown as embedded in ceramic plate [17]. However, it would be apparent to one of ordinary skill in the art that the ceramic ring [18] of FIG. 9 could be used instead of the ceramic plate [17].

What I claim is:

1. A process for measuring the temperature of a metallic workpiece and its solid content in a partially solidified state, characterised in that the workpiece is sent a reference signal which turns into a measurement signal in an exploring coil situated near the workpiece;

the measurement signal is compared with the reference signal;

the reference signal is induced by an induction coil which serves to heat and surround the workpiece;

a phase shift between these two signals is defined and/or a quotient is defined from the amplitude-related values of the two signals;

a calibration curve relating to the inter-dependence between the phase shift and/or the value of the quotient on the one hand and the temperature and the percentage of solid matter in this type of workpiece on the other hand is plotted applying conventional methods; and finally, in another workpiece of this type, the temperature and the percentage of solid matter are calculated from the phase shift and/or the value of the quotient by referring to the calibration curve.

2. A process in accordance with claim 1, characterised in that the quotient is determined from the effective values of the two signals.

3. A process in accordance with claim 1, characterised in that the workpieces are metallic blocks made from a thixotropic alloy, which are processed in a partially solidified state.

4. A process in accordance with claim 1, characterised in that the incoming frequency of the reference signal lies between 50 Hz and 10 kHz.

5. A process in accordance with claim 1, characterised in that the reference signal is kept constant.

6. A process in accordance with claim 1, characterised in that the voltage induced in the exploring coil is selected to serve as the exploring coil signal.

7. A process in accordance with claim 1, characterised in that the reference signal is derived from a heating coil current.

8. A process in accordance with claim 2, characterised in that the workpieces are metallic blocks made from a thixotropic alloy, which are processed in a partially solidified state.

9. A device for measuring the temperature of a metallic workpiece and its solid content in a partially solidified state, said device comprising a reference coil (4), an exploring coil (2), and an electronic unit for comparing the signals from the reference coil (4) and the exploring coil (2), characterised in that the reference coil (4) serves as an induction coil which surrounds and heats the workpiece (3), and that the exploring coil (2) is embedded in fireproof material to safeguard it against mechanical stress and mechanical displacement and is mounted on a support which can be positioned so that the workpiece (3) is within the field of the induction coil.

10. A device in accordance with claim 9, characterised in that the support includes a front surface for pushing the heated workpiece into a casting chamber, said exploring coil (2) being mounted in a ceramic plate (17) or a ceramic ring (18) which is embedded in said front surface.

11. A device in accordance with claim 9, characterised in that the exploring coil (2) is integrated within said support (1).

12. A devise in accordance with claim 9, characterised in that the exploring coil (2) is arranged within an electrical insulator, positioned as closely as possible to the front of the workpiece (3).

13. A device in accordance with claim 9, characterised in that the exploring coil (2) is thermally insulated against the workpiece (3).

14. A device in accordance with claim 9, characterised in that the turns of the exploring coil (2) are arranged within the profile of the workpiece (3).

15. A device in accordance with claim 13, characterised in that the turns of the exploring coil (2) are arranged at a constant distance from the contour of the front of the workpiece (3) within the profile of this front.

16. A device in accordance with claim 13, characterised in that the exploring coil (2) is formed by a single or a multiple ring-shaped wire coil.

17. A device in accordance with claim 10, characterised in that the exploring coil (2) is integrated within said support (1).

* * * * *